US008992076B2

(12) United States Patent
Bahr

(10) Patent No.: US 8,992,076 B2
(45) Date of Patent: Mar. 31, 2015

(54) DILATOMETER FOR MEASURING METALLIC SAMPLES

(75) Inventor: Heinz-Ludwig Bahr, Bad Oeynhausen (DE)

(73) Assignee: Waters GmbH, Eschborn (DE)

( * ) Notice: Subject to any disclaimer, the term of this patent is extended or adjusted under 35 U.S.C. 154(b) by 0 days.

(21) Appl. No.: 13/541,047

(22) Filed: Jul. 3, 2012

(65) Prior Publication Data

US 2012/0275486 A1 Nov. 1, 2012

(30) Foreign Application Priority Data

Dec. 15, 2010 (DE) .......... 10 2010 061 247
Jul. 5, 2011 (DE) .......... 10 2011 051 561

(51) Int. Cl.
*G01N 25/16* (2006.01)
*G01B 9/02* (2006.01)

(52) U.S. Cl.
CPC ............ *G01N 25/16* (2013.01)
USPC .......... 374/56; 356/485

(58) Field of Classification Search
USPC .......... 374/55
See application file for complete search history.

(56) References Cited

U.S. PATENT DOCUMENTS

| | | | | |
|---|---|---|---|---|
| 3,805,589 A | * | 4/1974 | Clusener et al. | 374/56 |
| 5,080,495 A | * | 1/1992 | Hashimoto et al. | 374/43 |
| 5,362,151 A | * | 11/1994 | Ollivier et al. | 374/55 |
| 5,479,261 A | * | 12/1995 | Hansen | 356/628 |
| 6,761,480 B2 | * | 7/2004 | Parnicza et al. | 374/179 |
| 6,767,127 B2 | * | 7/2004 | Paganelli | 374/55 |
| 7,118,272 B2 | * | 10/2006 | Bobenhausen | 374/55 |
| 7,524,105 B2 | * | 4/2009 | Baehr | 374/55 |
| 2002/0136262 A1 | * | 9/2002 | Feger | 374/55 |
| 2003/0108082 A1 | | 6/2003 | Paganelli | |
| 2008/0043803 A1 | * | 2/2008 | Bandoh | 374/100 |
| 2010/0208242 A1 | | 8/2010 | Martinez et al. | |

FOREIGN PATENT DOCUMENTS

| | | |
|---|---|---|
| DE | 30 26 298 | 4/1981 |
| DE | 10309284 A1 | 9/2004 |
| DE | 10 2006 019 434 | 10/2007 |
| DE | 102006019433 A1 | 10/2007 |
| EP | 0 482 294 | 4/1992 |
| EP | 0 537 038 | 4/1993 |

OTHER PUBLICATIONS

German Examination Report for Application No. 10 2011 051 561.5 filed Jul. 5, 2011.
Neubert H. et al., "A high-speed interferometric dilatometer", Measurement Science and Technology, vol. 20, (2009), pp. 1-5.
Ruban V. V. et al., "Noncontact strain gauge in a high-temperature dilatometer", Measurement Techniques, Consultants Bureau, No. 3, pp. 25-27, (1991).
European Search Report for 12173790.2, dated Oct. 23, 2012.

* cited by examiner

*Primary Examiner* — Laura Martin
*Assistant Examiner* — Nasir U Ahmed
(74) *Attorney, Agent, or Firm* — Waters Technologies Corporation

(57) ABSTRACT

A dilatometer for measuring metallic samples. The dilatometer includes a sample holder configured to receive and clamp a sample, an induction coil arranged on the sample, the induction coil configured to heat the sample, and a sensor for measuring the temperature of the sample.

6 Claims, 5 Drawing Sheets

DILATOMETER FOR MEASURING METALLIC SAMPLES

CROSS-REFERENCE TO RELATED APPLICATION

This application claims benefit of and priority to German Patent Application No. 10 2010 061 247.2-33, filed Dec. 15, 2010, the content of which Application is incorporated by reference herein.

BACKGROUND AND SUMMARY

The present disclosure relates to a dilatometer for measuring metallic samples.

There are dilatometers in which a metallic sample is clamped between two clamping pins in a longitudinal direction. The sample is heated up by an induction coil and the change in length is measured with the aid of the two clamping pins. In addition, the sample temperature is detected in a central region of the sample. A disadvantage of such a dilatometer is that heat is transferred out of the sample at the surfaces that are in contact with the clamping pins, thus resulting in a temperature gradient within the sample and so affecting the correlation between the measured temperature and the change in length. Particularly in the case of phase transformations being examined, this can lead to them not running simultaneously within the sample because the phase transformation, for example, in a central region, is already completed while it is just commencing in the peripheral regions. Asymmetries of the induction field additionally affect these temperature gradients negatively. In the case of such dilatometers, the measurements are afflicted with errors since the phase transition cannot be detected flawlessly, which is especially noticeable in the case of high heating up and cooling down rates.

The present disclosure includes a dilatometer for measuring metallic samples by which an exact measurement of the temperature-dependent change in length is achieved.

The exact measurement is achieved by a dilatometer that includes a sample holder configured to receive and clamp a sample, an induction coil arranged on the sample, the induction coil configured to heat the sample, a sensor for measuring the temperature of the sample, and an optical measuring device for detecting a change in a length of the sample.

As noted above, the dilatometer of the present disclosure includes an optical measuring device for detecting a change in length of the sample. This makes it possible to undertake a contact-free measurement of a change in length. Due to this contact-free measurement, no heat outflow takes place at the measuring point. Moreover, with the optical measuring device, the change in length can be detected with high accuracy.

According to an embodiment of the present disclosure, the optical measuring device detects a change in length in a measuring plane and the sensor for measuring the temperature of the sample measures the temperature in the region of this plane. As a result, an exact measurement of change in length can be carried out even in the case of a temperature gradient presenting in a longitudinal direction. That is because the measurement of the temperature takes place in the region of the measurement of change in length. Measuring the "length change" in this context does not necessarily mean a measurement in the longitudinal direction of a sample, but rather in any direction of the sample, for example, transverse to a longitudinal direction of the sample. The sensor can detect the temperature in the region of the measuring plane of the optical measuring device, wherein within the region a slight space between the sensor and the measuring plane is also covered. The slight space not adversely affecting the measurement.

According to a further embodiment of the present disclosure, the optical measuring device has a transmitter and a receiver and at least one sensor for measuring the temperature, which is situated in the shadow of the optical measuring device at the side of the sample facing towards or facing away from the receiver. In this way, a temperature measurement can take place exactly in the measuring plane, wherein the sensor does not interfere with the optical measuring device as it is situated in the shadow or at the side facing the transmitter. Only those peripheral regions of the sample being measured by the optical measuring device should be kept away from the sensor.

In the case of the optical measuring device, a light source with a collimator for producing a parallel beam path can be employed as a transmitter, according to the present disclosure. As a receiver, sensors can be used to detect the silhouette image of the sample, for example a high-speed linear CCD sensor. The sensor for measuring the temperature can therefore make contact with the sample in the "shadowed area" of the optical measuring device and so does not hinder the measurement of a change in length.

In an embodiment according to the present disclosure, the sensor is designed as a thermocouple that is fixed at the tip to the sample. Because of the small cross-section of the conductors of the thermocouples, these do not affect the temperature of the sample in any lasting manner.

The at least one induction coil may, for example, have a gap in a central region, and a measuring plane of the optical measuring device is situated in the region of this gap. This way, the measuring plane can be oriented perpendicular to a longitudinal direction of the sample, wherein merely the gradient of the induction coil in the region of the gap is increased slightly in order to provide space for a measuring plane of the optical measuring device. The at least one induction coil can, in accordance with the present disclosure, have arbitrary shapes. For example, circular coils are used, but also flat coils and specially adapted coils, which have a gap in the central region for the optical measuring device so that the measuring beam can detect the change in length of the sample without hindrance. Additionally, it is within the scope of the present disclosure to provide a helical induction coil with a uniform winding and to align the measuring plane essentially parallel to the gradient of the winding, so that the arrangement of a broader gap in the region of the induction coil can be dispensed with.

The sample holder may, for example, include two clamping pins and/or transmission rods, between which the sample can be clamped in a longitudinal direction. By way of the transmission rods, a length change in a longitudinal direction of the sample can also be detected. In addition, the optical measuring device can then carry out a measurement essentially perpendicular to the longitudinal direction.

Other aspects of the present disclosure will become apparent from the following descriptions when considered in conjunction with the accompanying drawings.

DETAILED DESCRIPTION

Figure 1:
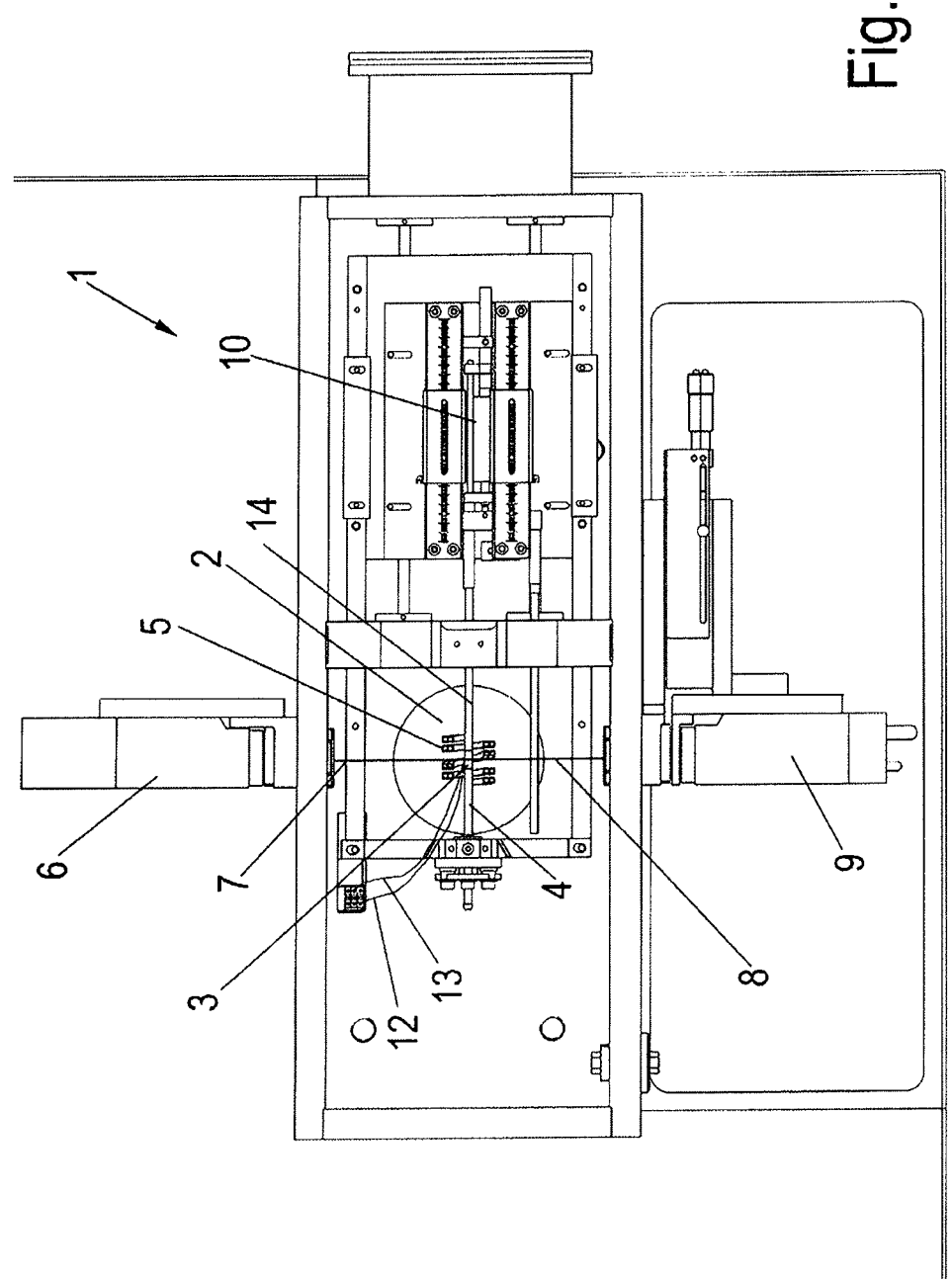
FIG. 1 shows a schematic view of a dilatometer, in accordance with the present disclosure.

A dilatometer 1 comprises a sample chamber 2 within a housing, wherein a metallic sample 3 is clamped in a sample holder that is formed by a first clamping pin 4 and a second clamping pin 14. The sample 3 can be a cylindrical rod, tube, square, polygon or other geometric shape. Hereinafter, the phrase "longitudinal direction" is understood to be the direction that extends along the longitudinal axis of the clamping pins 4 and 14.

The sample chamber 2 may include an inert gas and/or vacuum, may be thermally insulated, and may have other functionalities that are not further described here.

For measuring a length change of the sample 3, an optical measuring device is provided with a transmitter 6 and a receiver 9. The transmitter 6 comprises a light source, for example a high-power GaN LED, which emits light having a constant wavelength that is then directed at the sample 3 by an optical system having, for example, a collimator and a diffuser. In this manner, the transmitter 6 emits a band-shaped beam path 7 that is incident on the sample 3 in a central region of the sample 3, in a range between about 30% and 70% of the total length of the sample 3.

On the side facing away from the sample 3, a band-shaped beam path 8 is incident on the receiver 9, wherein the band-shaped beam path 8 projects a silhouette image of the sample 3 into the receiver 9. As the receiver 9, an optical sensor for exactly detecting the length of the sample 3 can be situated in the region of the measuring plane, wherein the measuring plane is formed by the band-shaped beam paths 7 and 8. The measuring plane of the optical measuring device is thereby arranged essentially perpendicular to the longitudinal direction of the clamping pins, or sample holders 4 and 14, respectfully.

Arranged around the sample 3 in the sample chamber 2, there is an induction coil 5 that extends in the longitudinal direction beyond the sample 3. Via the induction coil 5, the sample 3 can, in accordance with the present disclosure be heated up at high speed, for example at over 1,000 K/s.

Furthermore, on heating up or cooling down the sample 3, a change in length in the longitudinal direction of the sample can be detected, as a displacement transducer 10 is provided that is connected to the second clamping pin 14. Thus, movement of the second clamping pin 14 is measured. The first clamping pin 4 is designed to be stationary.

Figure 2:
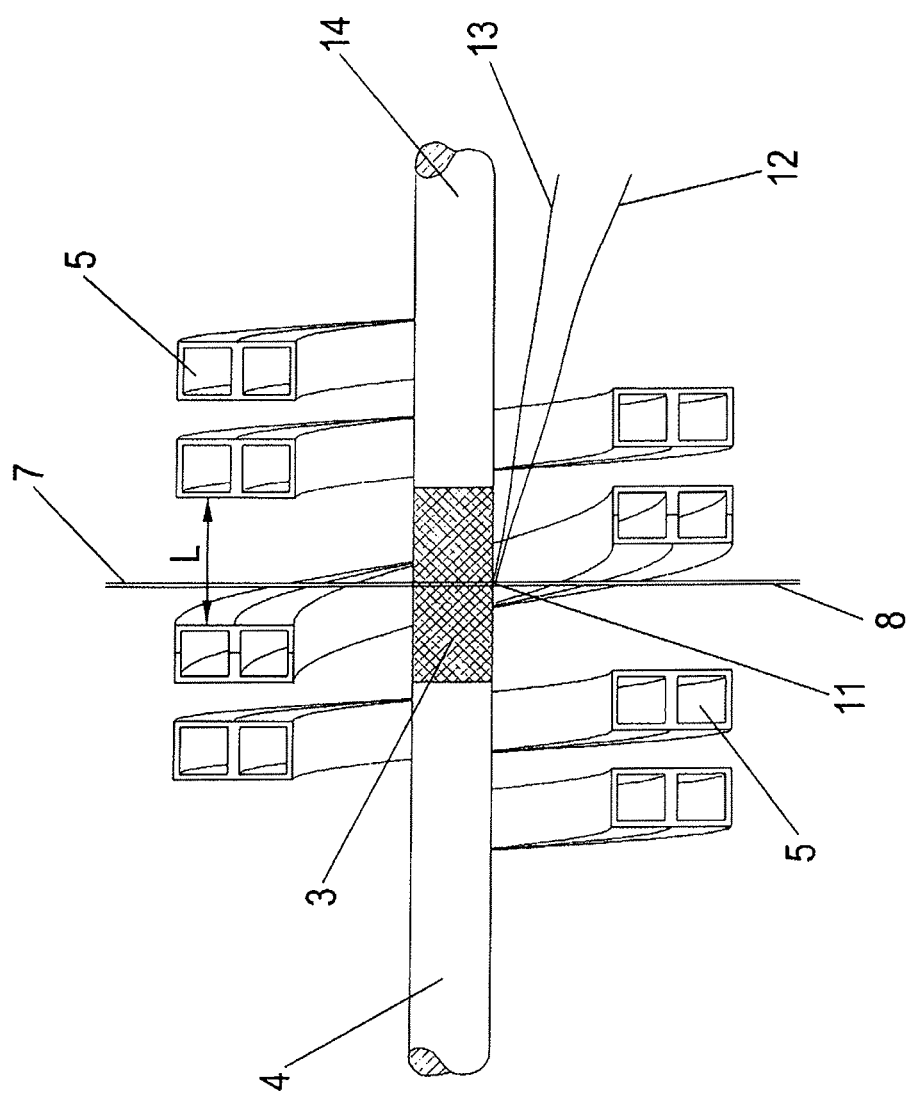
FIG. 2 shows an enlarged detailed view of the dilatometer of FIG. 1 in a region of the sample.

As shown in FIG. 2, a sensor 11, in the form of a thermocouple, is located on the sample 3. The sensor 11 is fixed at a tip to the sample 3, for example by spot-welding. The thermocouple 11 comprises a first conductor 12 and a second conductor 13, the cross-sections of which, relative to the sample 3, are designed to be very small so that heat loss via the conductors 12 and 13 is negligible.

The tip of the thermocouple 11 is arranged in a shadowed area of the sample 3 in a region of the measuring plane of the optical measuring device, the measuring plane facing the receiver 9. This way, the temperature of the sample 3 is detected relatively exactly at the position at which also the measurement of the change in length takes place via the optical measuring device. The temperature sensor 11 maybe, for example, arranged exactly in the region of the measuring plane.

For heating the sample 3, the induction coil 5 is wound around the sample 3. It is within the scope of the present disclosure that flat coils or other coil shapes suited to the situation can also be employed. In the region of the optical measuring device, or respectively, the measuring plane between two adjacent windings of the induction coil 5, a gap L is formed. In this gap L, the pitch of the winding is selected to be slightly larger so that the beam path 7 can incident in a plane on the sample 3 and that, in addition, the beam path 8 can be received by the receiver 9 without being influenced by a winding. It is within the scope of the present disclosure to align the measuring plane of the optical measuring device at a slight inclination via the beam paths 7 and 8 in order to reduce the gap L between two windings of the induction coil 5. Then the measuring plane would not be aligned exactly perpendicular to the longitudinal direction of the sample holder.

Figure 3:
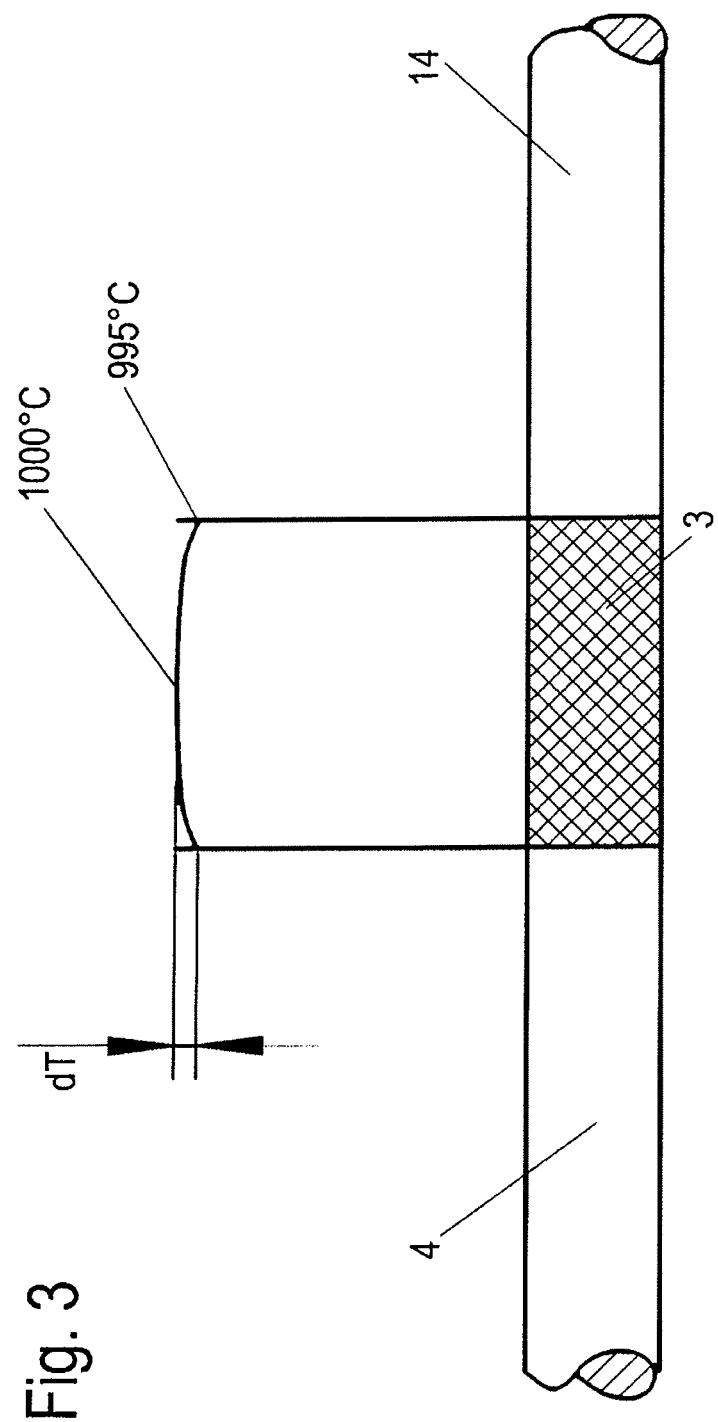
FIG. 3 shows an enlarged view of the sample in the region of a sample holder with a temperature profile, in accordance with the present disclosure.

As shown in FIG. 3, the sample 3 is clamped between the first clamping pin 4 and the second clamping pin 14 of the sample holder. The sample 3 is heated by the induction coil 5 and, as shown, the sample 3 has a temperature of 1,000° C. in a central area while in the edge regions there is a visible heat drain at the first clamping pin 4 and the second clamping pin 14 so that a temperature of 995° C. is present. In an embodiment of a dilatometer according to the present disclosure, this temperature difference dT cannot lead to inaccurate measurements because the measuring plane of the optical measuring device and the sensor for measuring the temperature of the sample are arranged in a central region of the sample 3 in which there is no further temperature loss at the sample holders 4 and 14. In this manner, an accurate temperature-dependent length change measurement can be achieved especially, for example, in the phase transition of a metallic sample, such as between high-temperature phase, austenite, and low-temperature phase, martensite.

Figure 4:
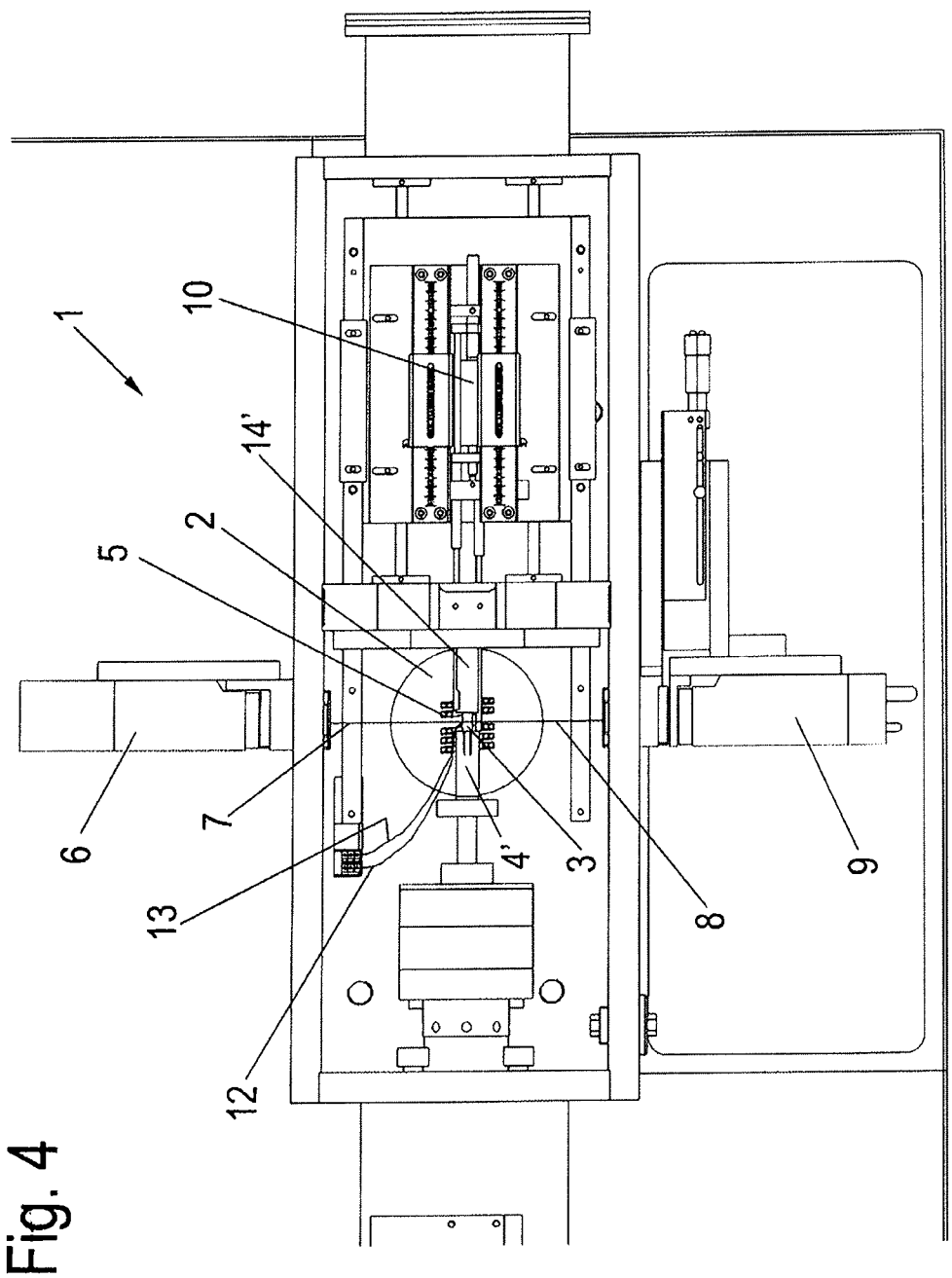
FIG. 4 shows a view of the dilatometer of FIG. 1 with a modified sample holder.
Figure 5:
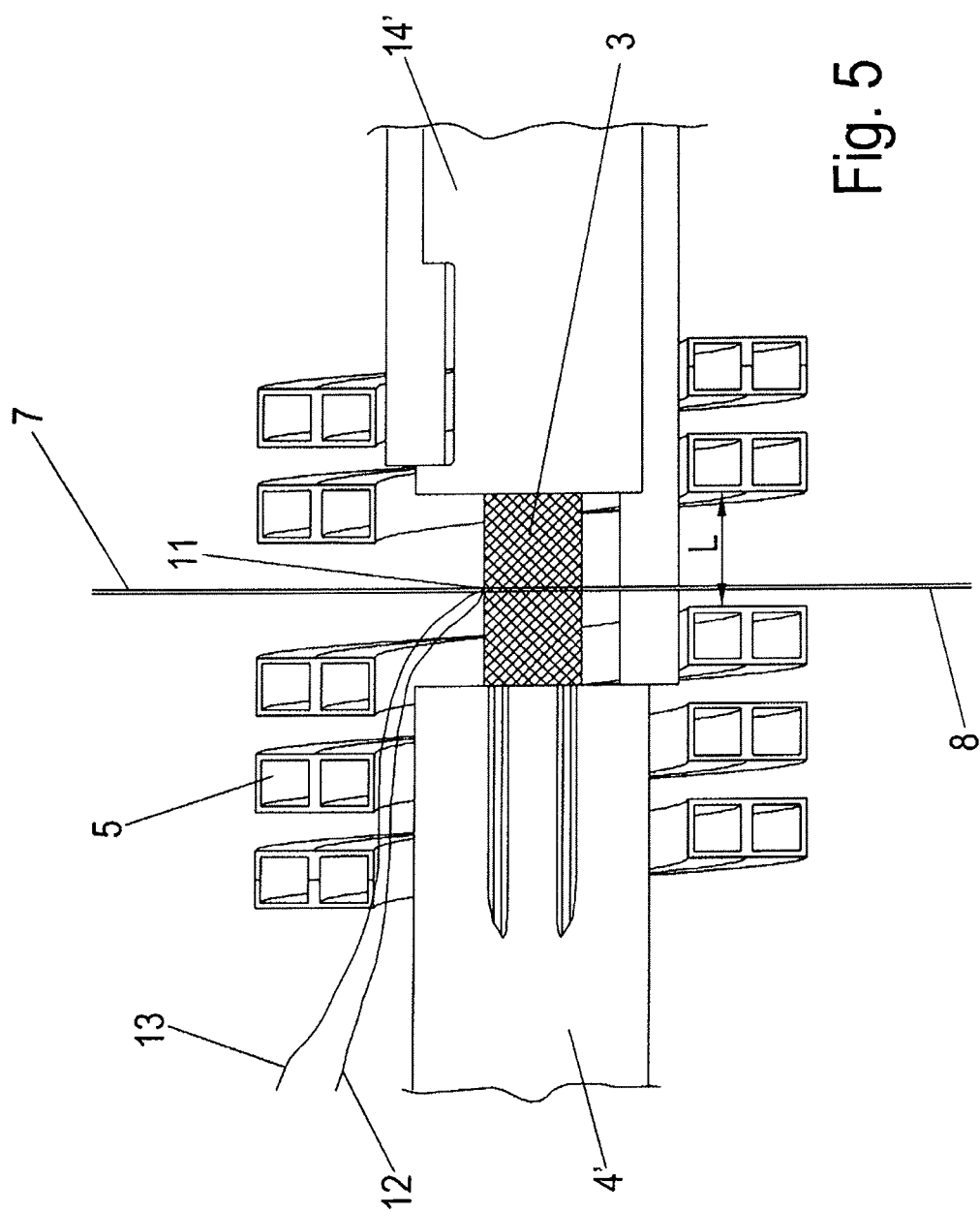
FIG. 5 shows a view of the dilatometer of FIG. 4 in the region of the sample.

While the dilatometer 1 is shown in FIGS. 1 and 2 in a quenching mode in which the sample 3 expands or contracts due to a temperature change, in FIG. 4 the dilatometer 1 of FIG. 1 is depicted in a deformation mode. In this embodiment of FIG. 4, the same components are designated with the same reference numbers but some have prime numbers. As sample holders in the deformation mode, a first clamping pin 4' and a second clamping pin 14' are employed that have a significantly larger cross-section in relation to the sample 3. This allows the sample 3 to be compressed at any particular temperature and following this, rapidly cooled down in order to, for example, generate a time-temperature-transformation diagram. Via the induction coil 5, the sample 3 can be heated up, while a flushing of the sample 3 with gas cools it down. A length change dependent on the temperature can be measured by the optical measuring device having the transmitter 6 and the receiver 9.

In the region of the measuring plane, a temperature sensor 11 is provided that is designed in accordance with FIG. 2 and that is arranged on the side of the transmitter 6, albeit in a middle area of the sample 3 and not in the edge regions that are detected by the optical measuring device.

Although the present disclosure has been described and illustrated in detail, it is to be clearly understood that this is done by way of illustration and example only and is not to be taken by way of limitation. The scope of the present disclosure is to be limited only by the terms of the appended claims.

I claim:

1. A dilatometer for measuring metallic samples, the dilatometer comprising:
   a sample holder including two clamping pins, the sample holder configured to receive and clamp a sample in a longitudinal direction between the two clamping pins;
   an induction coil arranged on the sample, the induction coil configured to heat the sample;
   a sensor for measuring the temperature of the sample; and
   an optical measuring device for detecting a change in a length of the sample, wherein a measuring plane of the optical measuring device is oriented substantially perpendicular to the longitudinal direction of the sample between the two clamping pins, wherein the measuring plane of the optical measuring device is between windings of induction coil.

2. The dilatometer according to claim 1, wherein the optical measuring device detects a change in length of the sample in a measuring plane of the optical measuring device and the sensor measures the temperature of the sample exactly in a region of the measuring plane.

3. The dilatometer according to claim 1, wherein the optical measuring device includes a transmitter and a receiver, and the sensor for measuring the temperature is in contact with the sample at a side facing the receiver.

4. The dilatometer according to claim 1, wherein the sensor is formed as a thermocouple that is fixed at a tip to the sample.

5. The dilatometer according to claim 1, wherein the at induction coil has a gap in a central region and a measuring plane of the optical measuring device is arranged in a region of the gap.

6. The dilatometer according to claim 1, wherein the sample holder is configured to detect a change in length of the sample in a longitudinal direction.

* * * * *